US011701247B2

(12) United States Patent
Madore

(10) Patent No.: US 11,701,247 B2
(45) Date of Patent: Jul. 18, 2023

(54) RESIN-BASED MALE CHASTITY DEVICE UTILIZING ANTI-PULLOUTS AND MULTIPLE OVERMOLDED SYNTHETIC REGIONS AND COVERINGS

(71) Applicant: Austin Madore, Mulberry, FL (US)

(72) Inventor: Austin Madore, Mulberry, FL (US)

( * ) Notice: Subject to any disclaimer, the term of this patent is extended or adjusted under 35 U.S.C. 154(b) by 0 days.

(21) Appl. No.: 17/666,617

(22) Filed: Feb. 8, 2022

(65) Prior Publication Data

US 2022/0151811 A1 May 19, 2022

Related U.S. Application Data

(63) Continuation of application No. 16/633,199, filed as application No. PCT/US2019/059312 on Nov. 1, 2019, now abandoned.

(60) Provisional application No. 62/827,016, filed on Mar. 30, 2019, provisional application No. 62/776,923, filed on Dec. 7, 2018.

(51) Int. Cl.
*A61F 5/00* (2006.01)

(52) U.S. Cl.
CPC ................. *A61F 5/0096* (2013.01)

(58) Field of Classification Search
CPC combination set(s) only.
See application file for complete search history.

(56) References Cited

U.S. PATENT DOCUMENTS

| 995,600 | A | 6/1911 | Heyser | |
|---|---|---|---|---|
| 6,349,727 | B1 * | 2/2002 | Stewart, Jr. | A61F 2/0054 128/885 |
| 7,578,296 | B2 | 8/2009 | Miller et al. | |
| 8,007,431 | B2 | 8/2011 | Miller et al. | |
| 2010/0089406 | A1 * | 4/2010 | Kachiguina | A61F 6/206 128/842 |
| 2015/0216717 | A1 * | 8/2015 | Madore | A61F 6/02 128/883 |

OTHER PUBLICATIONS

Polycarbonate (PC) [Online], [retrieved on Nov. 16, 2022], Retrieved from the internet URL: https://www.bpf.co.uk/plastipedia/polymers/Polycarbonate.aspx#properties (Year: 2022).*
Silicone's Properties and Advantages for Molded and Extruded Rubber [online], [retrieved on Nov. 9, 2022], Retrieved from the internet URL: https://www.vanguardproducts.com/blog/silicone-properties/ (Year: 2022).*
The Synthetic Rubber Production Process [online], [retrieved on Nov. 16, 2022], Retrieved from the internet URL: https://www.aquasealrubber.co.uk/articles/the-synthetic-rubber-production-process/#:~:text=Synthetic%20rubber%20is%20any%20man,polymers%20made%20from%20petroleum%20byproducts. (Year: 2020).*

* cited by examiner

*Primary Examiner* — Ophelia A Hawthorne
*Assistant Examiner* — Gina McCarthy
(74) *Attorney, Agent, or Firm* — William Lovin & Assoc., LLC; William R. Lovin

(57) ABSTRACT

A flexible male chastity device that may be permanently affixed to the scrotum and penis of the user and is substantially non-removable is disclosed. This device also includes a hinged insert or anti-pullout ring. Also, this device is constructed from ridged and flexible materials and includes multiple regions of overmolded synthetic coverings.

10 Claims, 3 Drawing Sheets

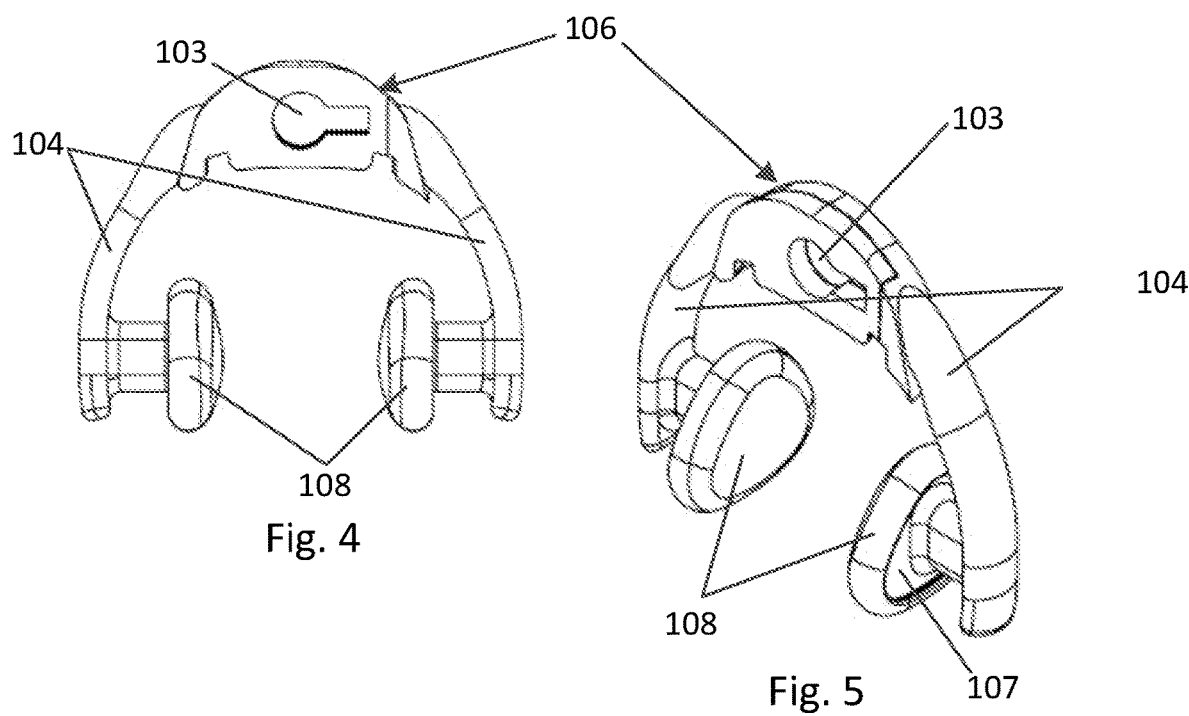

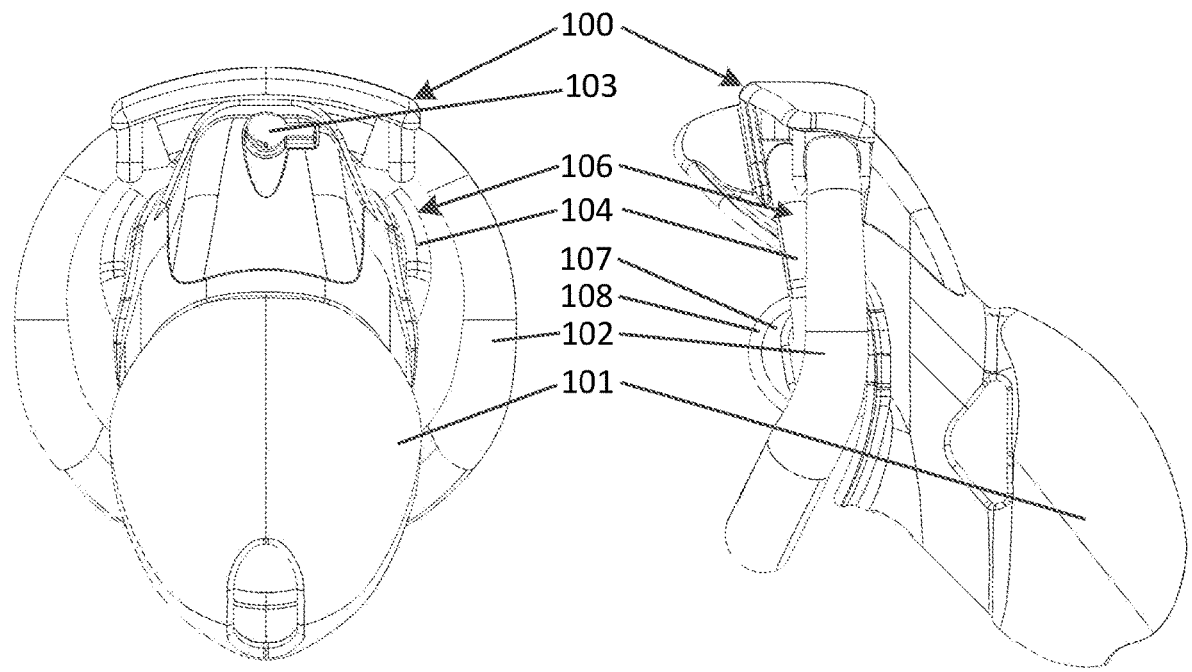
Fig. 6
Fig. 7
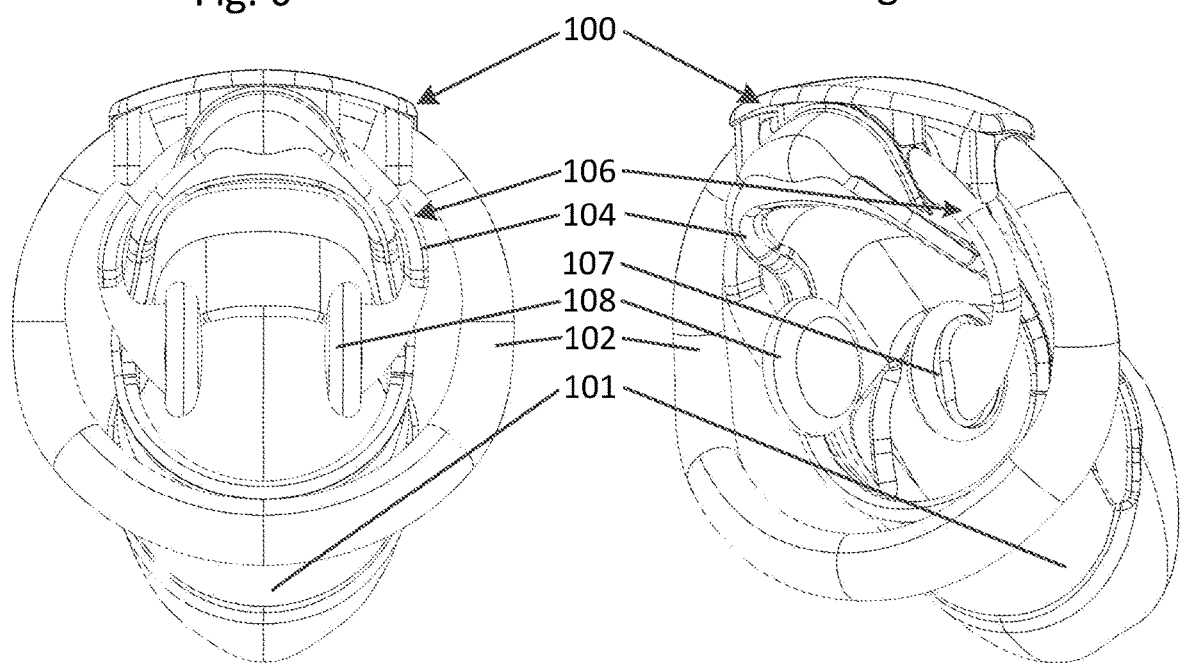
Fig. 8
Fig. 9

RESIN-BASED MALE CHASTITY DEVICE UTILIZING ANTI-PULLOUTS AND MULTIPLE OVERMOLDED SYNTHETIC REGIONS AND COVERINGS

CROSS-REFERENCE TO RELATED APPLICATIONS

This application is a continuation of U.S. Non-Prov. application Ser. No. 16/633,199 filed Jan. 23, 2020 which is a national stage entry of Patent Cooperation Treaty App. No. PCT/US19/59312 filed Nov. 1, 2019 which takes benefit of U.S. Prov. App. No. 62/827,016 filed Mar. 30, 2019 and U.S. Prov. App. No. 62/776,923 filed Dec. 7, 2018 and incorporates all of these, in their entirety, by reference.

FIELD OF THE INVENTION

A flexible male chastity device that may be permanently affixed to the scrotum and penis of the user and is substantially non-removable is disclosed. This device also includes a hinged insert or anti-pullout ring. Also, this device is constructed from ridged and flexible materials and includes multiple regions of overmolded synthetic coverings.

BACKGROUND OF THE INVENTION

The invention relates to a flexibly constructed male chastity device for protracted wear on the male sex organ to prevent sexual intercourse and masturbation.

In the prior art, a chastity belt is a locking item of clothing designed to prevent sexual intercourse and masturbation as well as to protect the wearer from sexual temptation. Chastity belts and related devices have a long human history. According to some, the chastity belt was used as an anti-temptation device during the Crusades. When the knight left for the Holy Lands on a Crusade, often his Lady would wear a chastity belt to preserve her faithfulness to him. Male chastity belts are also known in the prior art. U.S. Pat. No. 995,600 (Surgical Appliance) was developed, for example, to prevent masturbation by the mentally ill.

Modern devices range from simple leather or plastic toys commonly sold by adult stores to expensive high-security stainless steel devices. A chastity cage, also referred to as a "ball trap" device, is a device which encloses the male genitals to prevent stimulation and erection. Most such chastity cages have two parts: a ring seated around the base of the penis behind the scrotum and a capped tube, into which the flaccid penis is inserted. The tube is perforated to allow fluid to drain. Some designs have a curved or angled tube to make erections uncomfortable. Ordinarily, the two parts mate together on hinges or pins and are secured, usually with a padlock. When the device is locked, the testicles are trapped in the gap between the penis tube and the ring that is ostensibly narrow enough to prevent the testicles, and therefore the penis, from being pulled out. An exemplary device is disclosed in U.S. Pat. No. 7,578,296 (Male Chastity Apparatus, Method, and System) and its continuing application, U.S. Pat. No. 8,007,431 (Male Chastity Apparatus, Method, and System). Such chastity cage must be properly sized, fitted and adjusted in order to be secure and not cause physical damage. Unsurprisingly, ring size and spacing are the two most important adjustments that can be made. A ring that is too tight will cut off blood flow, potentially cause physical damage, and is extremely uncomfortable to wear while one that is too loose will not be secure.

Accordingly, a first embodiment of the present invention is directed towards a rigidly constructed male chastity device with a base structure constructed such that the scrotum may be pulled through the base. Such an apparatus eliminates the need for a hinged base structure while also eliminating the need for multiply sized versions of the same device.

A second embodiment of the present invention includes a rigid securing insert with hard, internally projecting hooks overmolded with a synthetic covering that can be attached over, and secured to, the flexible base structure.

SUMMARY OF THE INVENTION

In a first embodiment of the present invention, the flexible male chastity device comprises a ventilated cage housing comprising a shaft portion with a base configured to encase the shaft and the head of the penis. The base portion is generally circular, or horizontally oval when viewed from the rear, and is constructed of resin or hard plastic. Those having skill in the art will recognize that some, or all, of the base portion may be covered, or overmolded, with silastic or some other flexible, inert silicone elastomer such as rubber. The shaft portion is constructed of resin or hard plastic. The ventilated cage is worn such that the penis resides in the shaft portion and the base portion is insinuated behind the scrotum. Since the base portion is constructed of resin or hard plastic and is relatively inflexible, the base is placed behind the scrotum by stretching the scrotum to go through the base.

A second embodiment of the present invention is a hingedly interconnectable insert with two arms each with at least one anti-pullout projection, capable of mating with, and surrounding the aforementioned ventilated cage housing such that the anti-pullout projections extend into the central lumen of the cage housing causing a snug, secure fit of the base portion, its attached shaft portion, and the hinged insert around the penis of the user when the hinged insert is in its closed and locked position. The hinged insert further comprises a lower arc wherein the lower arc is affixed by molding, or some other equivalent means, and interconnects, the ends of the two arms. The lower arc is constructed of resin or hard plastic and may be covered, or overmolded with silastic or some other flexible, inert silicone elastomer such as rubber.

The anti-pullout projections have generally triangular or ovoid ends in contact with and proximal to the penis wherein the ovoid ends are coated or overmolded with a synthetic material such as silastic or some other flexible, inert silicone elastomer such as rubber.

BRIEF DESCRIPTION OF THE DRAWINGS

FIG. 4 is a front view of one embodiment of the hinged insert or anti-pullout ring.

FIG. 5 is a front isometric view of one embodiment of the hinged insert or anti-pullout ring showing the covered or overmolded anti-pullout projections.

FIG. 6 is a front elevation of a second embodiment of the invention.

FIG. 7 is a side elevation of a second embodiment of the invention.

FIG. 8 is a rear elevation of a second embodiment of the invention.

FIG. 9 is a rear isometric view of a second embodiment of the invention.

DETAILED DESCRIPTION OF THE INVENTION

Figure 1:
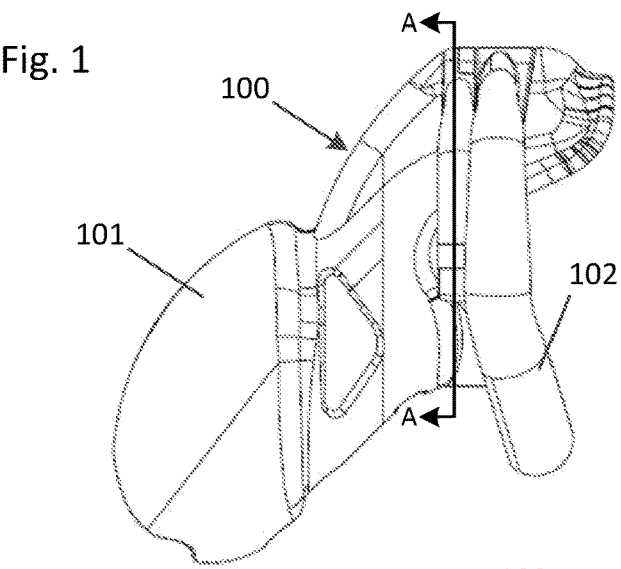
FIG. 1 is a side elevation of a first embodiment the invention.
Figure 2:
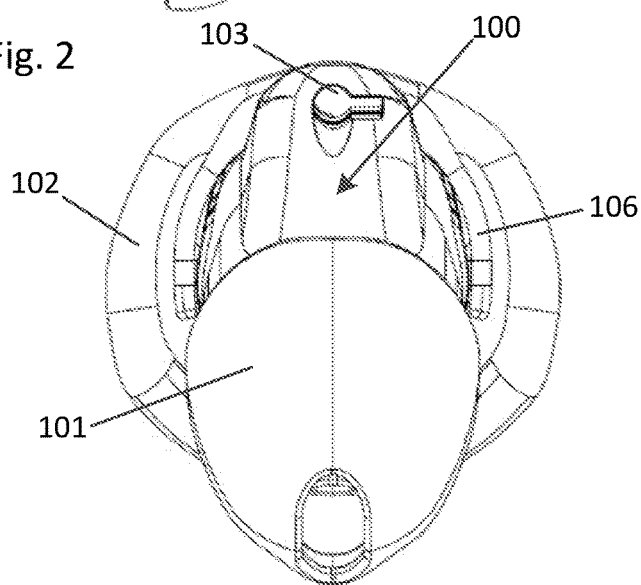
FIG. 2 is a front elevation of a first embodiment the invention.
Figure 3:
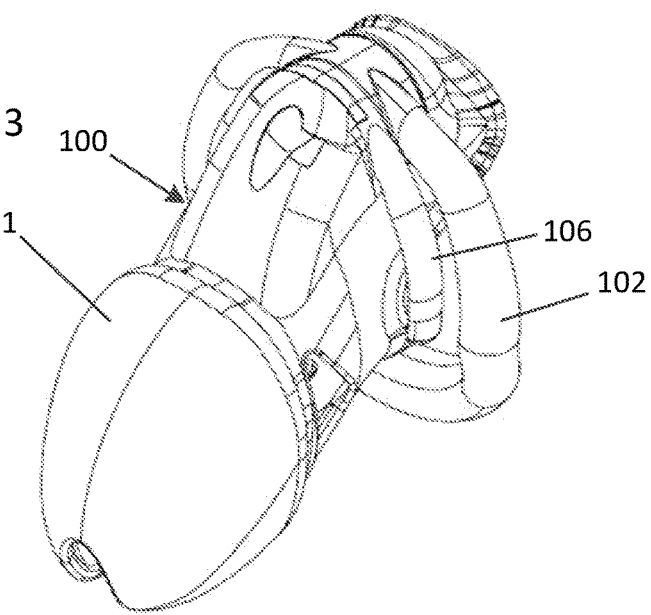
FIG. 3 is a front isometric view of a first embodiment the invention.

Turning now to FIGS. 1 through 3, a first embodiment of the present invention is a flexible male chastity device 100 comprised of a ventilated cage housing comprising shaft portion 101 with base portion 102 configured to encase the shaft and head of the penis. Base portion 102 is generally circular, or horizontally oval when viewed from the rear, and is constructed of resin or hard plastic. Those having skill in the art will recognize that some, or all, of base portion 102 may be covered, or overmolded, with silastic or some other flexible, inert silicone elastomer such as rubber. Shaft portion 101 and base portion 102 are worn such that the penis resides in shaft portion 101 and base portion 102 is insinuated behind the scrotum. Since base portion 102 is constructed of resin or hard plastic, base portion 102 is placed behind the scrotum by stretching and pulling the scrotum to go through the central lumen of base portion 102. This secures this first embodiment of the present invention to the body of the wearer.

Turning now to FIGS. 1 through 5, the first embodiment of the present invention also comprises a hingedly interconnectable insert or anti-pullout ring 106, with two arms 104, each with at least one anti-pullout projection 107. Arms 104 of hingedly interconnectable insert or anti-pullout ring 106 surround and mate with base portion 102 of the first embodiment of the present invention at line A-A shown in FIG. 1 such that anti-pullout projections 107 extend in front of and into the lumen of base portion 102 of the present invention. This causes a snug, secure fit of base portion 102, its attached shaft portion 101, and hingedly interconnectable insert or anti-pullout ring 106 around the penis of the user when hingedly interconnectable insert or anti-pullout ring 106 is in its closed and locked position. Anti-pullout projections 107 have generally triangular or ovoid ends in contact with, and proximal to, the wearer's skin wherein the generally triangular or ovoid ends are coated or overmolded with synthetic material 108 such as silastic or some other flexible, inert silicone elastomer such as rubber. Synthetic material grips the skin of the user adhering the present invention to the penis and scrotum of the user.

When worn, the user inserts a tabbed lock shaft from the rear through lockway 103 collinearly formed in base portion 102, its attached shaft portion 101, and hingedly interconnectable insert or anti-pullout ring 106. The tabbed lock shaft has an enlarged planar or ovoid base at the rear end and a transversely drilled hole at the front end. The bail of the padlock or other locking device is passed through the transversely hole drilled or molded in the exposed front end of the lock shaft. The padlock is locked to secure the device to wearer. Alternately, an insertable tabbed lock shaft may be inserted from the front of lockway 103 collinearly formed in base portion 102, its attached shaft portion 101, and hingedly interconnectable insert or anti-pullout ring 106. The insertable tabbed lock shaft may be locked and unlocked using a key from the front.

Turning now to FIGS. 6 through 9, a second embodiment of the present invention is a flexible male chastity device 100 comprised of a ventilated cage housing comprising shaft portion 101 with base portion 102 configured to encase the shaft and head of the penis. Base portion 102 is generally circular, or horizontally oval when viewed from the rear, and is constructed of resin or hard plastic. Those having skill in the art will recognize that some, or all, of base portion 102 may be covered, or overmolded, with silastic or some other flexible, inert silicone elastomer such as rubber. Shaft portion 101 and base portion 102 are worn such that the penis resides in shaft portion 101 and base portion 102 is insinuated behind the scrotum. Since base portion 102 is constructed of resin or hard plastic, base portion 102 is placed behind the scrotum by stretching and pulling the scrotum to go through the central lumen of base portion 102. This secures this embodiment of the present invention to the body of the wearer.

The second embodiment of the present invention also comprises a hingedly interconnectable insert or anti-pullout ring 106, with two arms 104, each with at least one anti-pullout projection 107. Arms 104 of hingedly interconnectable insert or anti-pullout ring 106 surround and mate with base portion 102 of the second embodiment of the present invention as detailed in FIG. 9 such that anti-pullout projections 107 extend behind and into the lumen of base portion 102 of the present invention. This causes a snug, secure fit of base portion 102, its attached shaft portion 101, and hingedly interconnectable insert or anti-pullout ring 106 around the penis of the user when hingedly interconnectable insert or anti-pullout ring 106 is in its closed and locked position. Anti-pullout projections 107 have generally triangular or ovoid ends in contact with, and proximal to, the wearer's skin wherein the generally triangular or ovoid ends are coated or overmolded with synthetic material 108 such as silastic or some other flexible, inert silicone elastomer such as rubber. Synthetic material grips the skin of the user adhering the present invention to the penis and scrotum of the user.

When worn the user inserts an insertable tabbed lock shaft through lockway 103 collinearly formed in base portion 102, its attached shaft portion 101, and hingedly interconnectable insert or anti-pullout ring 106 from the front. The insertable tabbed lock shaft may be locked and unlocked using a key from the front.

The invention claimed is:

1. A flexible male chastity device comprising a ventilated cage housing comprising:
   a) a shaft portion configured to surround a shaft and a head of a penis;
   b) a base portion configured to surround the shaft of the penis wherein the base portion is constructed of resin or hard plastic; and
   c) a hinged insert or anti-pullout ring configured to incompletely surround the shaft of the penis when worn comprising two hingedly interconnected arms each with at least one inwardly directed anti-pullout projection each most distant terminal end;
      1) wherein at least an outermost portion of each anti-pullout projection is coated with a flexible, inert silicone elastomer, and
      2) wherein the anti-pullout projections contact the skin of the penis or scrotum when the arms are worn on the shaft of the penis.

2. The flexible male chastity device of claim 1 wherein the device is configured to be locked to the body of the user.

3. The flexible male chastity device of claim 2 wherein the device is configured to be locked to the body of the user by means of a padlock.

4. The flexible male chastity device of claim 1 wherein the flexible, inert silicone elastomer is rubber.

5. The flexible male chastity device of claim 1 wherein the hingedly interconnected arms each with at least one inwardly directed anti-pullout projection at the most distant terminal end are oriented to lie in front of the base portion when the hingedly interconnected arms are worn on the shaft of the penis.

6. A flexible male chastity device comprising a ventilated cage housing comprising:
   a) a shaft portion;
   b) a base portion wherein the base portion is constructed of resin or hard plastic; and
   c) a hinged insert or anti-pullout ring configured to incompletely surround the shaft of the penis when worn comprising two hingedly interconnected arms each with at least one inwardly directed anti-pullout projection each most distant terminal end;
      1) wherein at least an outermost portion of each anti-pullout projection is coated with a flexible, inert silicone elastomer, and
      2) wherein the anti-pullout projections do not contact each other when worn on the shaft of a penis.

7. The flexible male chastity device of claim 6 wherein device is configured to be locked to the body of the user.

8. The flexible male chastity device of claim 7 wherein device is configured to be locked to the body of the user by means of a padlock.

9. The flexible male chastity device of claim 6 wherein the flexible, inert silicone elastomer is rubber.

10. The flexible male chastity device of claim 6 wherein the hingedly interconnected arms each with at least one inwardly directed anti-pullout projection at the free end is oriented to lie in front of the base portion when the hingedly interconnected arms are worn partially surrounding the shaft of the penis.

* * * * *